(12) United States Patent
Sparks et al.

(10) Patent No.: US 8,062,588 B2
(45) Date of Patent: Nov. 22, 2011

(54) ULTRASONIC SANITATION DEVICE AND ASSOCIATED METHODS

(75) Inventors: David W. Sparks, Thonotosassa, FL (US); Roy Beckett, Orlando, FL (US)

(73) Assignee: Zimek Technologies IP, LLC, Orlando, FL (US)

( * ) Notice: Subject to any disclaimer, the term of this patent is extended or adjusted under 35 U.S.C. 154(b) by 349 days.

(21) Appl. No.: 11/277,176

(22) Filed: Mar. 22, 2006

(65) Prior Publication Data

US 2007/0224079 A1  Sep. 27, 2007

(51) Int. Cl.
A61L 2/00 (2006.01)
A61L 2/18 (2006.01)
A61L 9/00 (2006.01)
A61L 2/04 (2006.01)
A61L 11/00 (2006.01)
C23F 11/00 (2006.01)
B01J 19/00 (2006.01)

(52) U.S. Cl. ............ 422/28; 422/1; 422/20; 422/291; 422/292

(58) Field of Classification Search ............ 422/20, 422/127, 293, 128, 306, 1, 28, 291, 292
See application file for complete search history.

(56) References Cited

U.S. PATENT DOCUMENTS

| 1,929,234 | A |   | 10/1933 | Anderson |
| 2,876,083 | A | * | 3/1959 | Prietl ..................... 23/295 R |
| 3,559,427 | A |   | 2/1971 | Baker |
| 3,561,444 | A |   | 2/1971 | Boucher |
| 3,729,138 | A |   | 4/1973 | Tysk |
| 3,828,773 | A |   | 8/1974 | Buch et al. |
| 4,137,258 | A |   | 1/1979 | Moore et al. |
| 4,366,125 | A |   | 12/1982 | Kodera et al. |
| 4,385,911 | A |   | 5/1983 | Popeil et al. |
| 4,410,139 | A |   | 10/1983 | Nishikawa et al. |
| 4,517,159 | A |   | 5/1985 | Karlson |
| 4,731,204 | A |   | 3/1988 | Noma et al. |
| 5,017,199 | A | * | 5/1991 | Etchepare ................. 95/267 |

(Continued)

FOREIGN PATENT DOCUMENTS

DE  3414245 A * 10/1985

(Continued)

OTHER PUBLICATIONS

English machine translation of JP 11-123357.*

(Continued)

Primary Examiner — Sean E Conley
Assistant Examiner — Regina Yoo
(74) Attorney, Agent, or Firm — Allen, Dyer, Doppelt, Milbrath & Gilchrist, P.A.

(57) ABSTRACT

A device for sanitizing a space includes a tank having an interior space for holding an aqueous sanitizing liquid. A reactor vessel is supported within the interior space and above a bottom of the tank. A liquid depth in the tank interior space is maintained at a level beneath a top edge of the reactor vessel. An ultrasonic head comprising an ultrasonically vibratable disc for generating ultrasonic energy is positionable within and beneath the top edge of the reactor vessel. Liquid is transferrable from the tank interior space to the reactor vessel to a level for substantially submerging the ultrasonic head. The disc is vibrated to form an atomized fog of particles from the aqueous sanitizing liquid. The formed atomized fog is exhausted from the reactor vessel to a space exterior of the tank. A sanitizing composition is also provided.

15 Claims, 4 Drawing Sheets

U.S. PATENT DOCUMENTS

| | | | |
|---|---|---|---|
| 5,300,260 | A | 4/1994 | Keshet et al. |
| 5,611,967 | A | 3/1997 | Jane et al. |
| 5,645,769 | A | 7/1997 | Tamaru et al. |
| 5,653,919 | A | 8/1997 | White et al. |
| 5,783,117 | A * | 7/1998 | Byassee et al. ............... 261/29 |
| 5,868,999 | A * | 2/1999 | Karlson ........................ 422/30 |
| 5,878,355 | A | 3/1999 | Berg et al. |
| 6,102,992 | A | 8/2000 | Berg et al. |
| 6,244,576 | B1 | 6/2001 | Tsai |
| 6,245,361 | B1 * | 6/2001 | Merritt .......................... 424/665 |
| 6,379,616 | B1 | 4/2002 | Sheiman |
| 6,379,633 | B1 | 4/2002 | Garlick |
| 6,537,494 | B2 | 3/2003 | Garlick |
| 6,589,481 | B1 | 7/2003 | Lin et al. |
| 6,682,606 | B2 | 1/2004 | Walker |
| 6,685,895 | B1 | 2/2004 | Lin |
| 6,814,071 | B2 | 11/2004 | Klimowicz et al. |
| 7,145,052 | B1 | 12/2006 | Watkins |
| 7,524,454 | B1 | 4/2009 | Sparks |
| 2003/0031588 | A1* | 2/2003 | Schur ............................. 422/28 |
| 2003/0042629 | A1 | 3/2003 | Eom |
| 2003/0127535 | A1 | 7/2003 | Adiga et al. |
| 2003/0127753 | A1* | 7/2003 | Bachert ......................... 261/81 |
| 2003/0143110 | A1 | 7/2003 | Kritzler et al. |
| 2004/0005240 | A1 | 1/2004 | Adiga et al. |
| 2004/0009094 | A1* | 1/2004 | Adiga et al. .................... 422/28 |
| 2004/0022673 | A1 | 2/2004 | Protic |
| 2004/0022695 | A1* | 2/2004 | Simon et al. .................. 422/128 |
| 2004/0057866 | A1 | 3/2004 | Zumeris et al. |
| 2004/0101572 | A1* | 5/2004 | Kepner et al. ................. 424/617 |
| 2004/0146425 | A1 | 7/2004 | Joshi |
| 2005/0031486 | A1* | 2/2005 | Mole et al. ..................... 422/28 |
| 2005/0074359 | A1 | 4/2005 | Krieger et al. |
| 2005/0118939 | A1* | 6/2005 | Duescher ..................... 451/527 |
| 2005/0212152 | A1 | 9/2005 | Reens |
| 2005/0214386 | A1 | 9/2005 | Shaheen et al. |
| 2005/0220665 | A1 | 10/2005 | Ding |
| 2006/0162667 | A1* | 7/2006 | Papadoyianis et al. ....... 119/223 |
| 2006/0213508 | A1 | 9/2006 | Murray et al. |
| 2006/0216214 | A1 | 9/2006 | Brown et al. |
| 2006/0289490 | A1 | 12/2006 | Mielnik |
| 2007/0193132 | A1 | 8/2007 | Roscioli |
| 2008/0118396 | A1* | 5/2008 | De Meulenaer et al. ....... 422/20 |
| 2008/0193650 | A1 | 8/2008 | Lyon |

FOREIGN PATENT DOCUMENTS

| | | | |
|---|---|---|---|
| EP | 0571316 | | 11/1993 |
| EP | 1288584 | | 5/2003 |
| JP | 58072000 A | * | 4/1983 |
| JP | 8313019 | | 11/1996 |
| JP | 08313019 A | * | 11/1996 |
| JP | 09119685 A | * | 5/1997 |
| JP | 11-123357 | | 5/1999 |
| JP | 11123357 A | * | 5/1999 |
| JP | 2003-214664 | | 7/2003 |
| JP | 2003214664 A | * | 7/2003 |

OTHER PUBLICATIONS

English machine translation of JP 2003-214664.*
English translation of Abstract of JP 58-072000 from Derwent.*
U.S. Appl. No. 60/582,390, filed Jun. 23, 2004.*
English machine translation of JP 08313019 A.*
English machine translation of JP 9119685 A.*
English machine translation of Abstract fo DE 3414245 A.*

* cited by examiner

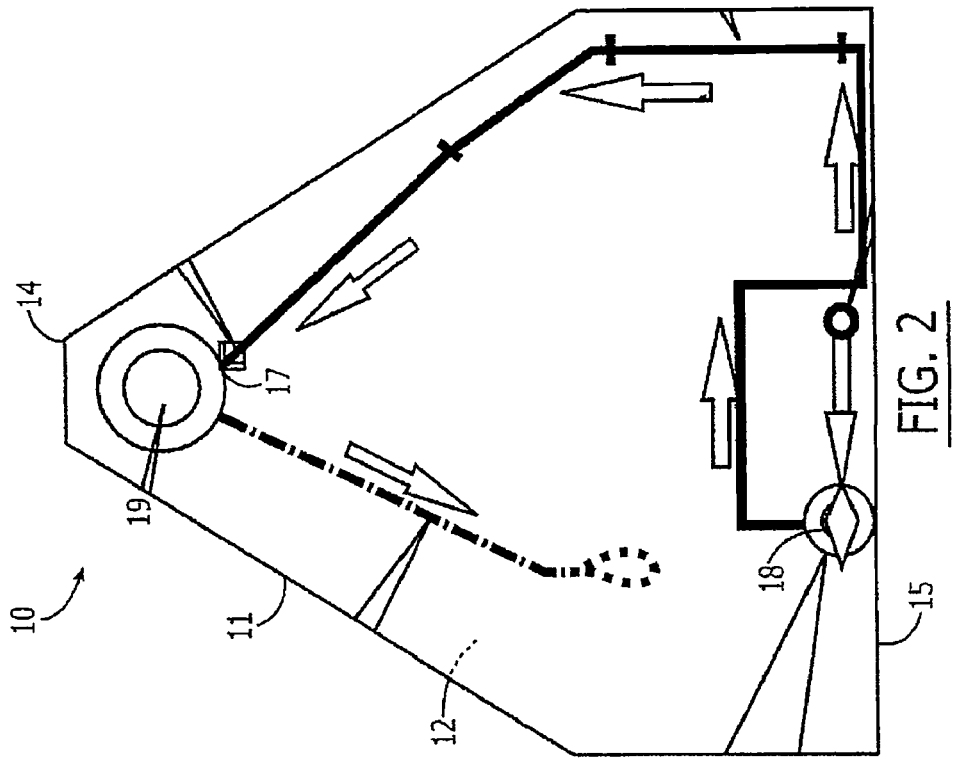
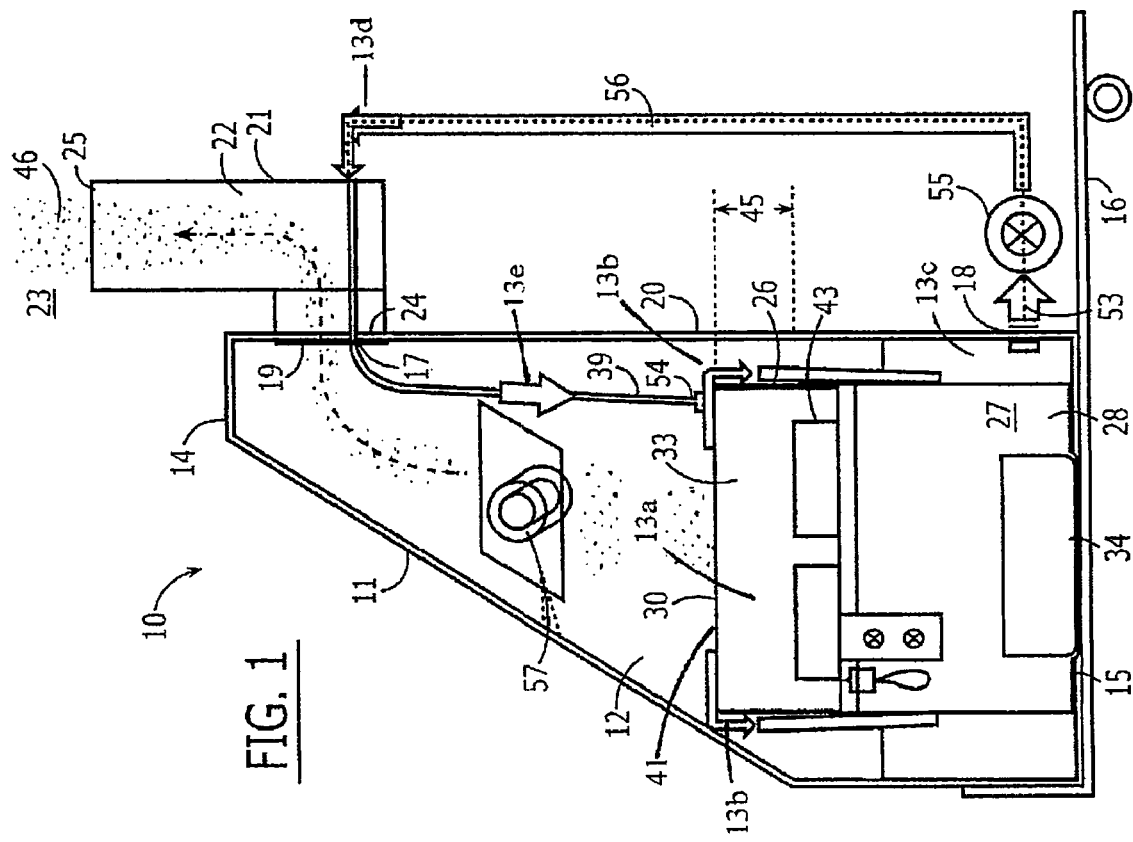

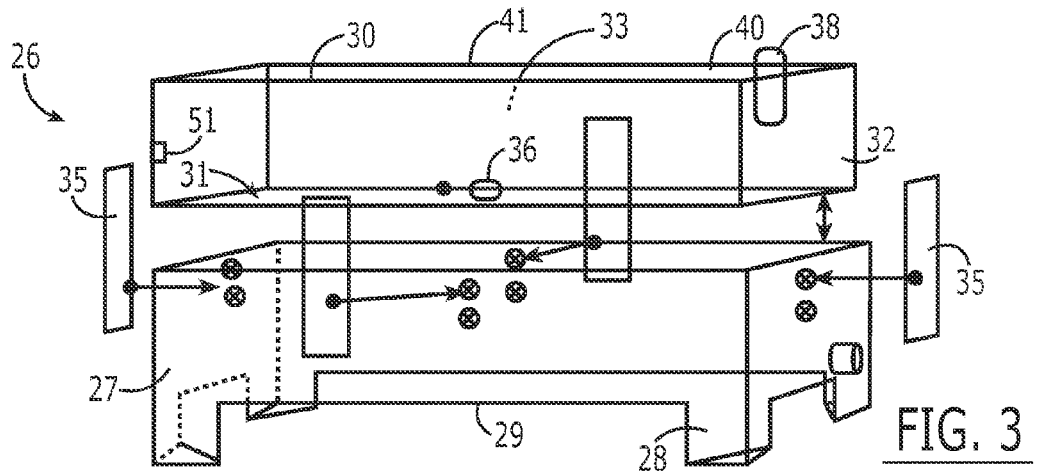
FIG. 3
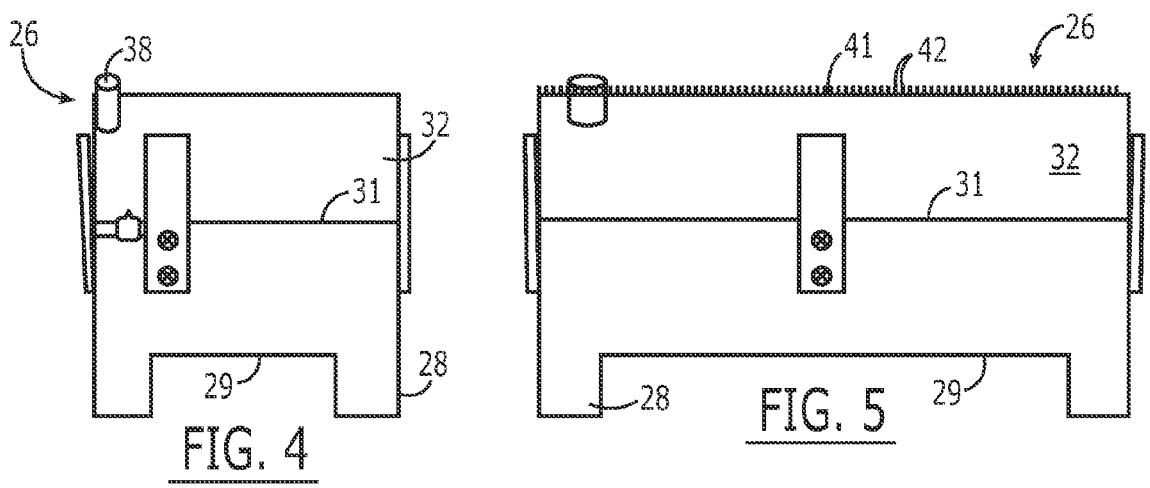
FIG. 4
FIG. 5
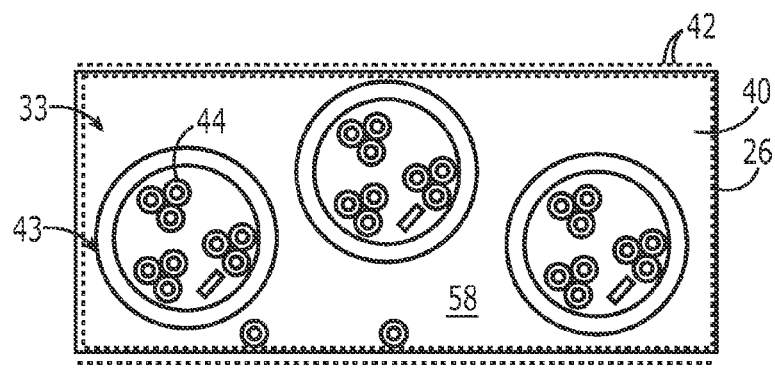
FIG. 6

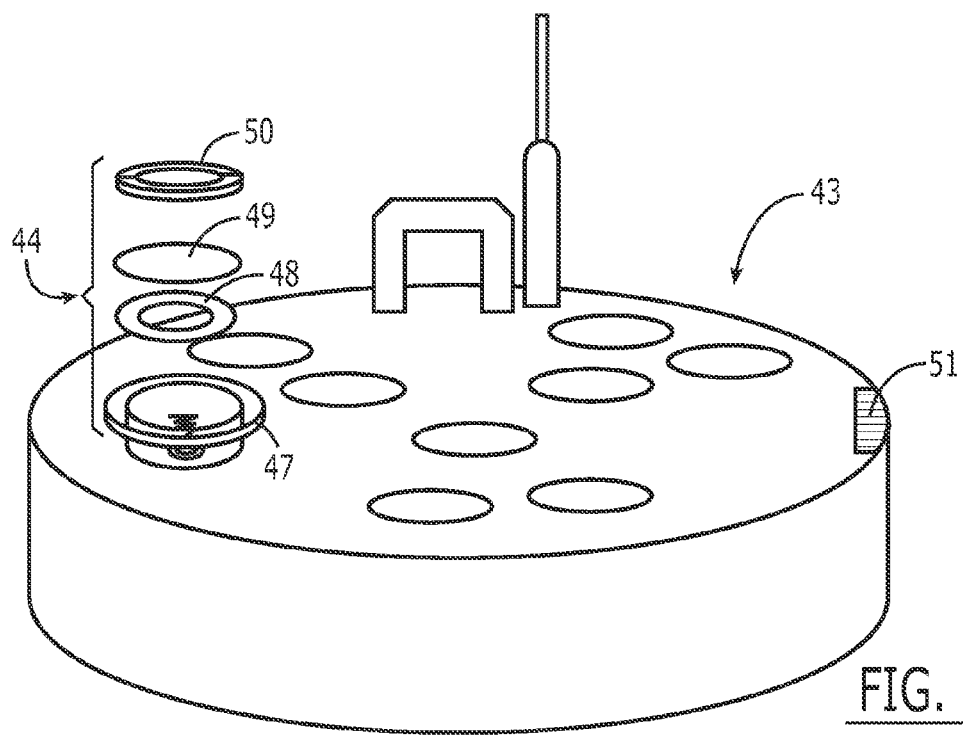
FIG. 7
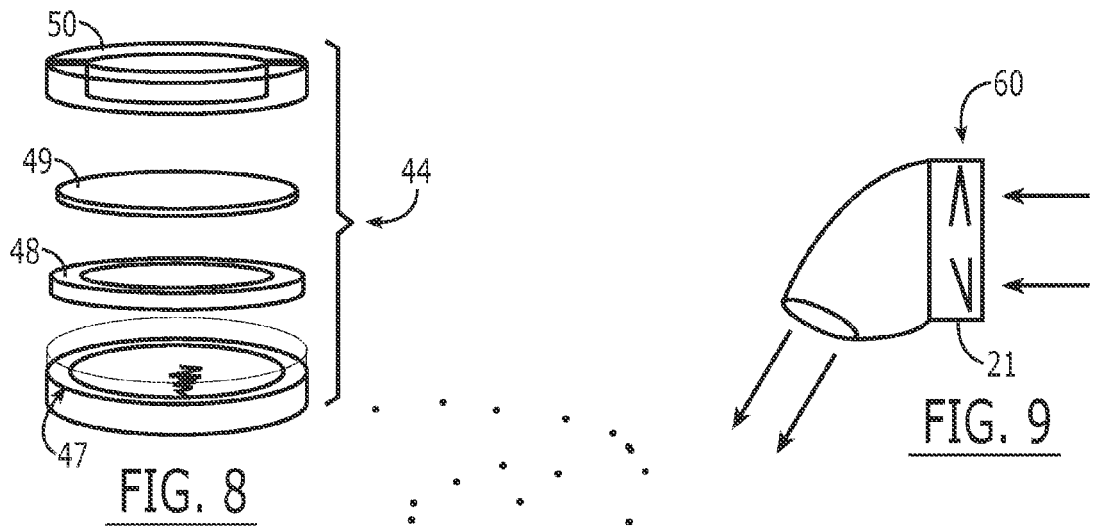
FIG. 8
FIG. 9
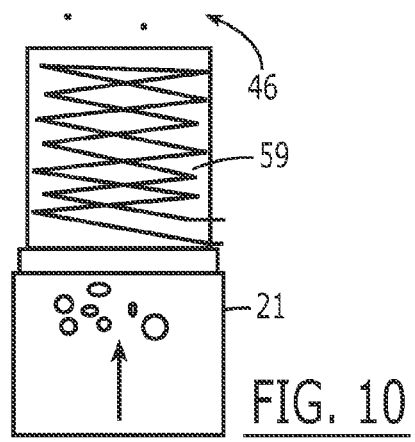
FIG. 10

ULTRASONIC SANITATION DEVICE AND ASSOCIATED METHODS

BACKGROUND OF THE INVENTION

1. Field of the Invention

The present invention relates to systems and methods for sanitizing enclosed spaces, and, more particularly, to such systems and methods that are capable of treating spaces three-dimensionally.

2. Description of Related Art

The sanitization and disinfection of enclosed spaces has become an issue of increasing importance owing to the possible presence of both natural and deliberately introduced contaminants. Since most commercial buildings are "sealed," that is, their windows cannot be opened, circulation of "fresh" air is typically not possible within a particular room. Similarly, most houses are now effectively sealed, with mostly processed air being circulated. In addition, some forms of conveyance, especially airplanes, are of necessity sealed against the environment during flight.

The enclosed nature of modern spaces has led to such problems as "sick building syndrome," since molds and mildews can flourish in enclosed, damp environments, and also to the possibility of the deliberate introduction of more insidious threats to life, such as biological and chemical agents.

At present most sanitizing and disinfecting agents are "two-dimensional," that is, they are applied to accessible surfaces. For example, when cleaning a table, typically the cleanser is applied to the table top, but not the underside.

"Fogging" agents are known for eradicating pests such as fleas and other insects. Ionization-type purifiers are also known in the art that use electrostatic means to collect allergens and pollutants.

Therefore, it would be beneficial to provide a more effective device, system, and method for sanitizing enclosed spaces in a three-dimensional fashion.

SUMMARY OF THE INVENTION

The present invention provides a device for sanitizing a space. The device comprises a tank having an interior space for holding an aqueous sanitizing liquid. A reactor vessel is supported within the interior space and above a bottom of the tank. Means are provided for maintaining a liquid depth in the tank interior space to a level beneath a top edge of the reactor vessel. An ultrasonic head comprising an ultrasonically vibratable disc for generating ultrasonic energy is positionable within and beneath the top edge of the reactor vessel. Means are included for transferring liquid from the tank interior space to the reactor vessel to a level for substantially submerging the ultrasonic head. Means are also provided for vibrating the disc to form an atomized fog of particles from the aqueous sanitizing liquid. Further means are provided for exhausting the formed atomized fog from the reactor vessel to a space exterior of the tank.

The device may also be used to distribute a liquid by creating the atomized fog as above and directing the fog to a desired location, for example, for delivering fertilizer or pesticide to a plot of land, for watering plants, or for distributing a skin-care product to the skin of a user, although these uses are not intended to be limiting.

The device of the present invention is able to reach all areas in a space where air can penetrate, and, since the atomized particles have been found to remain airborne longer than conventional mists, treatment is more thorough, and less chemical is required than used by previously known devices. A typical room of dimensions 12×12×10 ft can be disinfected in 10 min or less, for example.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is a side cross-sectional view of an embodiment of the sanitizing device of the present invention.

FIG. 2 is a rear view of the device of FIG. 1.

FIG. 3 is an exploded perspective view of the reactor tray of the device of FIG. 1.

FIG. 4 is a side view of the reactor tray.

FIG. 5 is a rear view of the reactor tray.

FIG. 6 is a top view of the reactor tray with ultrasonic heads positioned therein.

FIG. 7 is a side-top perspective view of an ultrasonic reactor head, with one disk seen in exploded view.

FIG. 8 is an exploded view of a reactor head disk.

FIG. 9 is a side perspective view of an alternate embodiment of an exhaust system including a diverter element.

FIG. 10 is a side cross-sectional view of an alternate embodiment incorporating a heating exhaust.

DETAILED DESCRIPTION OF THE PREFERRED EMBODIMENTS

Figure 11A:
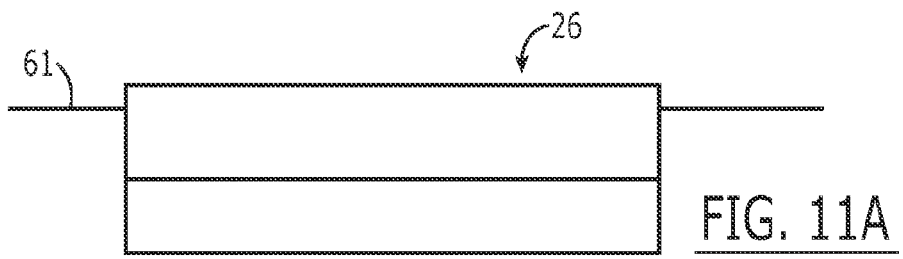
FIGS. 11A-11D are side cross-sectional views of different exemplary embodiments of the reactor tray.
Figure 11B:
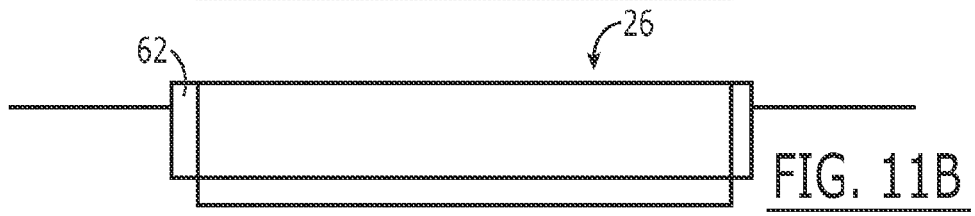
Figure 11C:
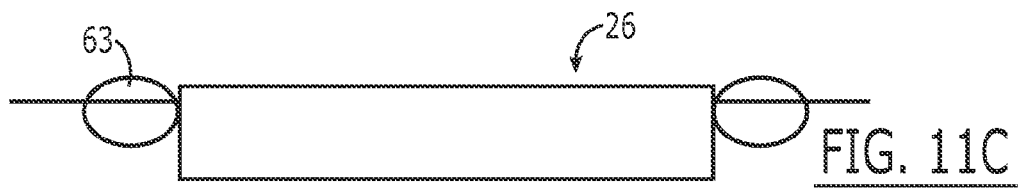
Figure 11D:
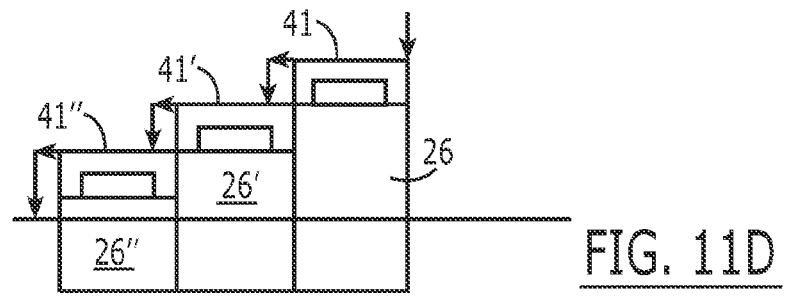
Figure 12:
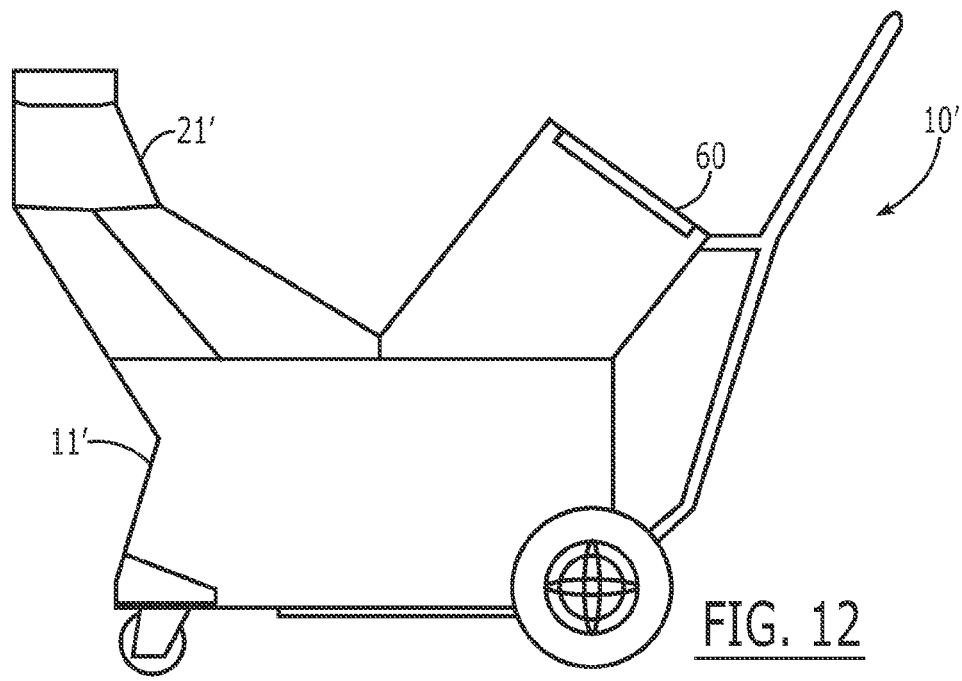
FIG. 12 is a schematic illustration of a side view of a device having a differently shaped tank.

A description of the preferred embodiments of the present invention will now be presented with reference to FIGS. 1-12. The device 10 for sanitizing a space includes a tank 11 (FIGS. 1 and 2) that has an interior space 12 for holding an aqueous sanitizing liquid 13. In a particular embodiment, the tank's top end 14 is substantially smaller than its bottom 15. Further, the tank 11 may be configured for placement upon a wheeled cart 16 for ease of transport.

The tank 11 has a liquid line aperture 17 adjacent the top 14 and a liquid outlet 18 adjacent the bottom 15. The tank 11 can comprise a material adapted to maintain a static charge, such as, but not intended to be limiting, a high-density polyethylene (HDPE) material.

A fog outlet 19 is positioned adjacent the tank's top 14 along the rear wall 20, and is in fluid communication with a chimney 21 having a bore 22 therethrough leading to a space 23 exterior of the tank 11. In a preferred embodiment, the chimney bore 22 has an elbow therein, shown by the dotted line in FIG. 1, meeting the fog outlet 19 at a first end 24 and the exterior space 23 at the second, upwardly directed end 25.

A reactor vessel 26 is supported within the tank's interior space 12 and above the tank's bottom 15. In a particular embodiment illustrated in FIGS. 3-5, not intended to be limiting, the reactor vessel 26 comprises a substantially hollow rectangular lower section 27 that has a plurality of support legs 28 that extend from a bottom 29 thereof. An upper substantially rectangular section 30 comprises a bottom 31 and four enclosing walls 32 that extending upwardly from the upper section's bottom 31 and are adapted to contain liquid in the interior space 33 formed thereby. The lower 27 and the upper 30 sections are affixable together with the upper section 30 atop the lower section 27 and are positionable within the tank's interior space 12 with the support legs 28 contacting the bottom surface 34 of the tank's interior space 12. One of skill in the art will recognize that additional embodiments for the reactor tray 26 could be envisioned, and that the shape presented here in is intended to be exemplary only.

In a particular embodiment, not intended to be limiting, the reactor vessel 26 is formed in two parts 27,30 in order to permit insertion into a particular tank 11. Here the parts 27,30 are held together with the use of joiner clips 35 that are screwed onto the lower section 27 and serve to brace the sections 27,30 together. The reactor vessel 26 has one or more drain holes 36 extending from the interior space 33 of the reactor vessel 26 through to the tank's interior space 12 and is positioned adjacent the bottom 31 of the reactor vessel's interior space 33.

The reactor vessel 26 further has affixed thereto a hose clamp 38 for supporting a liquid line 39, which will be discussed in the following. The top surface 40 of the upper section 30 should preferably have an area substantially greater than the top 14 of the tank 11.

Another feature of the reactor vessel 26 is that the top edge 41 of the upper section 30 has a plurality of notches 42 therealong. These notches 42 have been found important in permitting liquid to pass therethrough, but to substantially prevent foam from passing therethrough, thus retaining foam within the upper section 30 and not permitting it into the return line 39.

Positioned within the reactor vessel's upper section 30 is a plurality of ultrasonic heads 43, here, three ultrasonic heads (FIGS. 6-8). Each of the heads 43 comprises a plurality, here, nine, vibratable discs 44 for generating ultrasonic energy. The heads 43 are positioned so as to be submersible within the reactor vessel 26, the submersion depth 45 optimized for production of an atomized fog 46 of particles from the liquid 13 therewithin. Preferably the fog 46 comprises negatively charged particles, which aid dispersal and space coverage. It has been found that the depth 45 of the liquid column and also the vibration frequency affects the focus of the sound waves. The signal for activating the discs 44 is transmitted from devices known in the art, such as by way of a manual switch or level sensor.

The ultrasonic heads 43 believed at the time of filing to represent a best mode of carrying out the invention comprise heads obtained from Sonaer Ultrasonics (Farmingdale, N.Y.). An exemplary head that can be used comprises part number T241, although this is not intended to be limiting. The fog 46 created by these heads 43 can contain particles in a range of 0.25-5.0 μm, although this is not intended to be limiting, as the size may be larger in some instances. Each of the discs 44 include a substantially toroidal O-ring seat 47, a Viton O-ring 48 seated on the O-ring seat 47, a ceramic disk 49 positioned atop the O-ring 48, and a substantially toroidal retaining ring 50 positioned in circumferentially retaining relation atop the ceramic disk 49. The discs 44 are known in the art to be supplied with silicone O-rings, but it has been found that the increased stiffness and chemical resistance of the Viton material is beneficial to the invention.

The drain hole 36 discussed above has been found to be beneficial in extending the life of the device 10 by keeping the heads 43 dry. A level sensor 51 can also be provided for automatically turning the heads 43 on and off depending upon the presence or absence of liquid. The level sensor 51 can be positioned either on the tank 11 or on the heads 43 themselves.

Means are included for transferring liquid from the tank's interior space 12 to the reactor vessel 26 to a level for substantially submerging the ultrasonic head 43. For this purpose is provided a liquid line 39 that is in fluid communication with the tank's liquid outlet 18 at an inlet end 53 and with the reactor vessel 26 at an outlet end 54. The liquid line 39 in this embodiment passes through the liquid line aperture 17 between the inlet end 53 and the outlet end 54, and is affixed to the reactor vessel 26 with the use of the hose clamp 38.

As illustrated with reference again to FIG. 1, a pump 55 is provided along the liquid line 39 that is operable to move liquid 13 through the liquid line 39 from the tank's interior space 12 beneath the reactor vessel 26 to the interior space 33 of the reactor vessel 26. The liquid 13 is pumped from the bottom 15 of the tank 11 through the liquid line 39 via a clear portion 56 and into the tank through the liquid line aperture 17 near the top end 14 of the tank. The liquid line outlet end 54 delivers the liquid into the upper section 30 of the reactor 26 allowing the upper section 30 to be filled with the liquid 13*a* and an overflow of liquid 13*b* (illustrated with arrows) to cascade over the edge 41 into the bottom 15 of the tank 11 wherein the liquid 13*c* is pumped through the liquid outlet as the liquid 13*d* through the clear line portion 56 and to the liquid line aperture 17 wherein the liquid 13*e* is delivered to the upper section 30 to repeat the cycle from liquid 13*a*. Preferably the liquid line 39 comprises a substantially clear material, so that a portion 56 of the liquid line 39 exterior of the tank 11 can thereby optionally serve as an indicator of a liquid level within the tank's interior space 12 when the pump 55 is not operating. The placement of the liquid line portion 56 outside the tank 11 has also proven beneficial in assisting in cooling the liquid upon its pathway to the reactor vessel 26. In addition, a filtration element may be added to eliminate contaminants along the liquid line 39.

The device 10 further includes means for exhausting the atomized fog 46 that is formed to an exterior of the tank 11. This can be accomplished, for example, with the use of a fan 57 positioned within the tank's interior space 12 above the reactor vessel 26 and positioned to direct the formed atomized fog 46 from a top surface 58 of liquid 13 in the reactor vessel 26 to the fog outlet 19.

An additional feature that may be provided in certain circumstances includes a means for heating the fog 46, which has been found to reduce the size of the fog particles. Such a heating means may comprise, for example, a coil 59 (FIG. 10) positioned along the exhaust path.

It will be understood by one of skill in the art that many variations on the embodiment discussed above may be contemplated. For example, the exhaust system may include a diverter element 60 as illustrated in FIG. 9.

In addition, various alternate means may be employed to support the ultrasonic heads 43, as shown in the flotation elements of FIGS. 11A-11C, wherein a foam floater 61 (FIG. 11A), a sealed air cavity 62 (FIG. 11B), or a floater ring 63 (FIG. 11C) may be used to support the tray 26 and the heads 43.

Further, the reactor tray 26 may include a plurality of reactor vessels 26,26'26" positioned adjacent each other, the top edge 41 of a first reactor vessel 26 above the top edge 41' of a second reactor vessel 26', and so on. In this embodiment the liquid transferring means is adapted to transfer liquid 13 into the first reactor vessel 26, thereby permitting a cascade of liquid from the first reactor vessel 26 into the second reactor vessel 26' and thence into the third reactor vessel 26" during operation.

The shape of the device as illustrated herein is not intended to be limiting. For example, in an alternate embodiment 10' shown in FIG. 12, the tank 11' may have a chimney 21' at the front of the tank, with a liquid inlet 60 toward the rear of the tank 11'.

Another important feature of the present invention includes the liquid composition used for sanitizing spaces, and a method of making this composition. The invention is not intended to be limited, however, to the precise composition and proportion of ingredients in the liquid.

In a preferred embodiment, the composition is made as follows: 40 gallons of clean, carbon-filtered water is added to a clean plastic or stainless steel vessel, and a mixer is turned on. 1 pound of sodium metasilicate pentahydrate is mixed into the water slowly, and mixing continues for 5 min. With the mixer still running, a clean plastic pail is used to remove 1 gal of mixed solution for use in a pre-blending step. 70 ml of SE25 (Wacker Chemie AG, Munich, Germany), a silicone-based antifoaming agent, is added to the pail, and mixed using a clean plastic rod until the solution is blended thoroughly. At this point the solution will appear to be a cloudy micro-emulsion. 60 ml of K-2 surfactant (Lonza Chemical Corporation, Switzerland), used as a molecular coupler, is mixed slowly into the micro-emulsion until thoroughly blended.

With the mixer running, the pre-blend is added back into the first vessel at a rate of 180 ml per min while the mixer is running, and the mixer continues to run after the pre-blend has been added. Into a clean 1000-ml beaker containing 700 ml distilled water, 2 oz of Palaklor-1103041 (Pylam Products Company, Inc., Tempe, Ariz.) is added. This substance comprises a dye base for its ultraviolet reflective traits and can be used as tracer. The Palaklor is not necessary for the sanitizing aspect of the inventive composition, and can therefore be omitted if a tracer is not desired in the mixture. The mixture is shaken for 1 min, and is then added to the first vessel with continued mixing.

Water is added to the first vessel to bring the volume up to 55 gal, and mixing continues for 15 min. When blending is complete, the mixture stands for 1 h prior to packaging. For use, the mixture is diluted 1:1 with water.

To the mixture may be added sanitizing, disinfectant, and/or insecticidal elements such as, but not intended to be limited to, di-N-alkyl($C_{8-10}$)—N,N-dimethylammonium chloride, N-alkyl($C_{10-12}$)dimethylammonium chloride, tetrasodium ethylenediamine tetraacetate, sodium ethanol, 2-propanol, pyrethrum, octylphenoxypolyethoxyethanol (a nonionic surfactant), quaternary ammonia, formaldehyde, and peroxide.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and composition illustrated and described herein are by way of example, and the scope of the invention is not limited to the exact details of construction, constituents, and proportion.

What is claimed is:

1. A method for sanitizing an enclosed space using an atomized fog of particles, the method comprising the steps of:

providing a tank having an interior space including a top portion and a bottom portion, wherein the top portion is substantially smaller than the bottom portion;

supporting a reactor vessel within the interior space and above the bottom portion, the reactor vessel having an opening including a top edge, wherein the opening in the reactor vessel is dimensioned substantially greater than the top portion of the tank;

positioning an ultrasonically vibratable disc having an ultrasonic head at a fixed position within the reactor vessel and below the top edge;

placing an aqueous sanitizing liquid into the interior space at the bottom portion;

transferring the aqueous sanitizing liquid from the bottom portion into the reactor vessel;

continuing the aqueous sanitizing liquid transferring for permitting the aqueous sanitizing liquid to continuously cascade over the top edge of the reactor vessel for maintaining a constant distance between a surface of the aqueous sanitizing liquid within the reactor vessel and the ultrasonic head, and thus maintaining a substantially constant immersion depth of the ultrasonic head within the aqueous sanitizing liquid carried by the reactor vessel;

vibrating the ultrasonically vibratable disc to generate ultrasonic energy, the ultrasonic head positioned within and beneath the top edge of the reactor vessel and submerged in the aqueous sanitizing liquid to form the atomized fog of particles from the aqueous sanitizing liquid;

positioning a fan above the surface of the sanitizing liquid for directing the atomized fog of particles;

directing the atomized fog of particles from the vessel toward the top portion of the tank; and exhausting only the atomized fog of particles from the top portion to the enclosed space exterior of the tank through an outlet of the tank.

2. The space-sanitizing method recited in claim 1, wherein the transferring step comprises pumping the sanitizing liquid through a liquid line in fluid communication with a liquid outlet in the tank at an inlet end and with the reactor vessel at an outlet end, the liquid line passing through a liquid line aperture adjacent a top of the tank between the inlet end and the outlet end.

3. The space-sanitizing method recited in claim 2, wherein the liquid line comprises a substantially clear material, and further comprising the step of using a portion of the liquid line exterior of the tank as an indicator of a liquid level within the tank interior space when the pump is not operating.

4. The space-sanitizing method recited in claim 1, further comprising the steps of monitoring a submersion level of the ultrasonic head and, if the ultrasonic head is not submerged, disabling the vibrating step.

5. The space-sanitizing method recited in claim 1, wherein the exhausting step comprises exhausting the atomized fog of particles through a chimney having a bore therethrough, the bore having a first end in fluid communication with the fog outlet and a second, generally upwardly directed end open to the tank exterior space.

6. The space-sanitizing method recited in claim 1, wherein the top edge of the reactor vessel has a plurality of notches therealong for permitting liquid to pass therethrough but for substantially blocking foam from passing therethrough.

7. The space-sanitizing method recited in claim 1, further comprising the step of permitting the sanitizing liquid in the reactor vessel to drain from the reactor vessel to the tank interior space when the atomized fog of particles is not being formed.

8. The space-sanitizing method recited in claim 1, further comprising the step of heating the formed atomized fog for reducing a size of the fog particles.

9. A method for sanitizing an enclosed space using an, atomized fog of particles, the method comprising the steps of:

placing an aqueous sanitizing liquid into an interior space of a tank, the aqueous sanitizing liquid comprising water, sodium metasilicate pentahydrate, a surfactant, and an antifoaming agent;

positioning an ultrasonically vibratable disc having an ultrasonic head within a reactor vessel and below a top edge thereof, the top edge forming an opening substantially larger than a top end of the tank;

supporting the reactor vessel within the tank interior space and above a bottom end of the tank;

transferring the sanitizing liquid from the tank interior space to the reactor vessel for permitting the sanitizing liquid in the reactor vessel to cascade over the top edge of the reactor vessel and into the bottom end of the tank interior space;

vibrating the ultrasonically vibratable disc of the ultrasonic head to generate ultrasonic energy, the ultrasonic head submerged within the transferred liquid to form the atomized fog of particles from the aqueous sanitizing liquid; and exhausting the formed atomized fog of particles from the reactor vessel within the tank toward the top end and into the enclosed space exterior of the tank.

10. The method recited in claim 9, further comprising the step of making the aqueous sanitizing liquid, the making comprising the steps of:

mixing sodium metasilicate pentahydrate into water to form a first solution;

removing a partial amount of the first solution;

mixing an antifoaming agent into the partial amount of the first solution to form a second solution;

adding a surfactant to the second solution;

adding the second solution into the remaining first solution to form a third solution; and adding a second antifoaming agent to the third solution.

11. A method for sanitizing an enclosed space using an atomized fog of particles, the method comprising the steps of:

providing a tank having a top end and an opposing bottom end;

filling the tank with a volume of sanitizing liquid to a preselected fluid level within the bottom end of the tank;

supporting a vessel within the tank such that an edge defining an opening of the vessel is spaced above the preselected fluid level, the opening spaced from and dimensioned substantially larger then the top end of the tank;

positioning an ultrasonic head within the vessel and below the edge;

continuously transferring the sanitizing liquid from the tank into the vessel to cause the sanitizing liquid within the vessel to cascade over the edge for maintaining a constant immersion depth of the ultrasonic head within the sanitizing liquid carried by the vessel;

vibrating the ultrasonic head to cause the atomized fog of particles to be emitted from the sanitizing liquid;

directing the atomized fog of particles toward the top end of the tank; and exhausting the atomized fog of particles from the top end into the enclosed space exterior the tank.

12. The method according to claim 11, wherein the edge of the vessel comprises a plurality of notches therealong, and wherein the method comprises permitting the sanitizing liquid to pass through the notches while substantially blocking foam from passing therethrough.

13. The method according to claim 11, wherein the transferring comprises pumping the sanitizing liquid through a liquid line carried outside the tank and in fluid communication between a bottom portion of the tank bottom and the vessel.

14. The method according to claim 11, wherein the ultrasonic head vibrating causes the atomized fog of particles to substantially comprise particles ranging in size from 0.25 µm-5.0 µm.

15. The method according to claim 11, wherein the ultrasonic head positioning within the vessel comprises positioning a plurality of ultrasonic heads within the vessel, each below the edge.

* * * * *